US006681957B1

(12) United States Patent
Green (10) Patent No.: US 6,681,957 B1
(45) Date of Patent: Jan. 27, 2004

(54) COLLAPSIBLE DISPENSING SYSTEM

(76) Inventor: Ronald D. Green, 13595 Cable Rd., Pataskala, OH (US) 43062

(*) Notice: Subject to any disclaimer, the term of this patent is extended or adjusted under 35 U.S.C. 154(b) by 0 days.

(21) Appl. No.: 10/196,003

(22) Filed: Jul. 17, 2002

(51) Int. Cl.[7] ................................................ B67D 5/56
(52) U.S. Cl. ...................... 222/135; 222/136; 222/137; 222/145.3; 222/327; 222/386; 222/386.5
(58) Field of Search ................................ 222/94, 145.1, 222/145.3, 145.5, 145.6, 326, 327, 386, 386.5, 398, 135, 136, 137

(56) References Cited

U.S. PATENT DOCUMENTS

| | | | | |
|---|---|---|---|---|
| 2,705,463 A | * | 4/1955 | Moore | 222/137 |
| 4,050,612 A | * | 9/1977 | Stone | 222/135 |
| 4,340,154 A | | 7/1982 | VanManen | |
| 4,366,919 A | * | 1/1983 | Anderson | 222/137 |
| 4,457,641 A | * | 7/1984 | Smith | 222/390 |
| 5,161,715 A | | 11/1992 | Giannuzzi | |
| 5,184,757 A | | 2/1993 | Giannuzzi | |
| 5,242,082 A | | 9/1993 | Giannuzzi | |
| 5,310,091 A | * | 5/1994 | Dunning et al. | 222/135 |
| 5,339,992 A | | 8/1994 | Barthomeuf et al. | |
| 5,722,829 A | | 3/1998 | Wilcox et al. | |
| 5,875,928 A | | 3/1999 | Muller et al. | |
| 6,056,164 A | * | 5/2000 | Wakayama | 222/327 |

* cited by examiner

*Primary Examiner*—Kenneth Bomberg
(74) *Attorney, Agent, or Firm*—Richard L Huff (57) ABSTRACT

A dispenser for simultaneously dispensing at least two viscous materials to be mixed. The dispenser contains an outer cartridge and an inner container. The cartridge has an open rear end having a rear thrust wall which will be pushed forward by the conventional dispensing gun. The cartridge has a front end containing a nozzle for connecting with a mixing nozzle. The container extends from the front end to the rear end and is made of telescoping sections. Viscous materials are present within the container and in the space between the wall of the container and the wall of the cartridge. As the rear thrust wall is pushed forward. the telescopic sections are captured in recesses of the rear thrust wall. More than one concentric container may be present.

8 Claims, 9 Drawing Sheets

COLLAPSIBLE DISPENSING SYSTEM

BACKGROUND OF THE INVENTION

1. Field of the Invention

The field of this invention relates to collapsible dispensing devices suitable for the dispensing of non-solid, viscous material.

2. Description of the Related Art

Cartridges for storing and dispensing viscous materials such as resins, sealing compositions, dental compositions, or insulation compositions are known in the art. Such cartridges generally comprise an outer casing containing at one end, an end piece which attaches to an applicator nozzle and at the other end, a rear thrust wall designed to slide toward the end piece and force the viscous material out of the nozzle. This sliding of the rear thrust wall is brought about by a piston which is generally an integral part of a manually operated device, usually in the form of a gun equipped with a rack or friction advance mechanism.

Some viscous products consist of several viscous components which must be mixed, in given proportions, only at the time of application. It is known in the art to store the viscous components in multiple containers inside cartridges in such a way that the advancing rear thrust wall will force the components through a single mixing nozzle whereby the components become mixed at the time of application.

U.S. Pat. No. 5,339,992 to Barthomeuf et al discloses a cartridge comprising an outer casing and an inner casing. Each casing holds a viscous component of a final product. The cartridge has a front end piece for receiving an application nozzle and a rear thrust wall which drives the components forward and through the nozzle when it is advanced.

U.S. Pat. Nos. 5,161,715, 5,184,757, and 5,242,082 to Giannuzzi disclose a double-barreled gun designed to inject a two-component epoxy composition. The gun contains two parallel barrels, each containing a foil pack containing viscous components of the final epoxy composition. The gun contains two front end pieces which are adapted to send the components into a mixing nozzle. The gun contains two pistons for urging the foil packs forward. As the foil packs are urged forward, cutting elements in the forward end of each barrel slit the foil packs and allow for the discharge of the stored components.

U.S. Pat. No. 5,722,829 to Wilcox et al. and U.S. Pat. No. 5,875,928 to Müller et al are similar to each other in that each of these references discloses a double-barreled cartridge capable of receiving two parallel containers containing viscous components which should be mixed only at the time of application. Each container empties into a front end piece which passes the viscous components to a mixing nozzle. Each container has a rear thrust wall which may be forced forward to expel the contents of the container into the front end piece.

U.S. Pat. No. 4,340,154 to VanManen discloses a dispensing container for viscous components wherein the dispenser contains a cartridge containing an accordion-type container. The container holds a first viscous component and the area between the container and the cartridge wall holds a second viscous material. Forward movement of the rear thrust wall pushes both viscous components through a common outlet opening.

While the above dispensing devices are in common use, these devices display qualities which require improvements. One problem is the difficulty of obtaining a range of ratios of the several components. Different end compositions require different ratios of the components. Many dispensers are capable of dispensing only a single ratio of the components. If a different ratio is required, a different type of dispenser must be obtained. Another problem exists with the degree of emptying of the several components. Not all of the above devices afford complete dispensing of the contained components. This leads to wasted materials and the possibility of disposal problems.

SUMMARY OF THE INVENTION

The inventor recognized the above problems and solved them by providing a dispenser which comprises a cartridge which fits common caulking guns and a container within the cartridge which may easily be obtained in a variety of sizes and which will provide for complete emptying of the ingredients. Additionally, more than one container may be used for those times when a composition comprising three or more components is to be produced.

The dispenser of the present invention comprises a dispensing cartridge for use with viscous materials which should not be combined until the time of application. The cartridge fits common dispensing guns, such as caulking guns. The cartridge has a front end piece for receiving a dispensing nozzle and a rear thrust wall which drives the contents forward when pushed by the piston of the dispensing gun. Within the cartridge, there is at least one telescopic container holding one of the viscous components. The telescopic containers may be easily produced in a variety of sizes, thus providing a ready availability of a range of ratios of the components. Also the telescopic containers allow for complete emptying of the contained components.

DESCRIPTION OF THE PREFERRED EMBODIMENTS

The invention will now be described with reference to the above drawing, like reference numerals referring to like parts throughout the description.

Referring to FIGS. 1–9, 14, and 14A, the dispenser 2 of the present invention comprising a cartridge 4 and a single container 6 will now be described.

The cartridge 4, which is preferably circular in cross-section, has a cylindrical side wall 8 having an inner surface 10, an outer surface 12, a rearward end 14, and a forward end 16. The forward end 16 has a closed periphery 18 and an open central nozzle 20 adapted to attach to a mixing nozzle (not shown). The cartridge 4 has an open rearward end 14 for receiving the piston of a dispensing gun (not shown). The cartridge 4 has a slidable rear thrust wall 22 which drives the contents of the dispenser 2 forward as the thrust wall 22 is forced forward by the piston. To ensure that there is no leakage of the viscous contents, the rear thrust wall 22 has the same diameter as the inner diameter of the cartridge 4 with a flared edge (not shown) to ensure a seal. Additionally, the rear thrust wall 22 may be made of plastic having a tendency to push against the side wall of the cartridge 4.

The container 6 has a forward end 24 which has a neck 26. The neck 26 fits snugly into an open spacer 28 which, in turn, fits into the open central nozzle 20 of the cartridge 4 in such a manner as to leave an open space 30 between the neck 26 of the container 6 and the open central nozzle 20 of the cartridge 4.

The container 6, which is preferably circular in cross-section, has a generally cylindrical side wall 32 having an inner surface 34, an outer surface 36, a rearward end 38, and a forward end 40. The container 6 is made up of multiple cylindrical sections 42 such that, as the length of the container 6 gets shorter, the sections 42 will telescope one inside the next. It is preferred that the most forward section 42 will have the largest diameter and that the rearward sections 42 telescope into the next forward sections 42 as this lessens the possibility of leakage.

Figure 14:
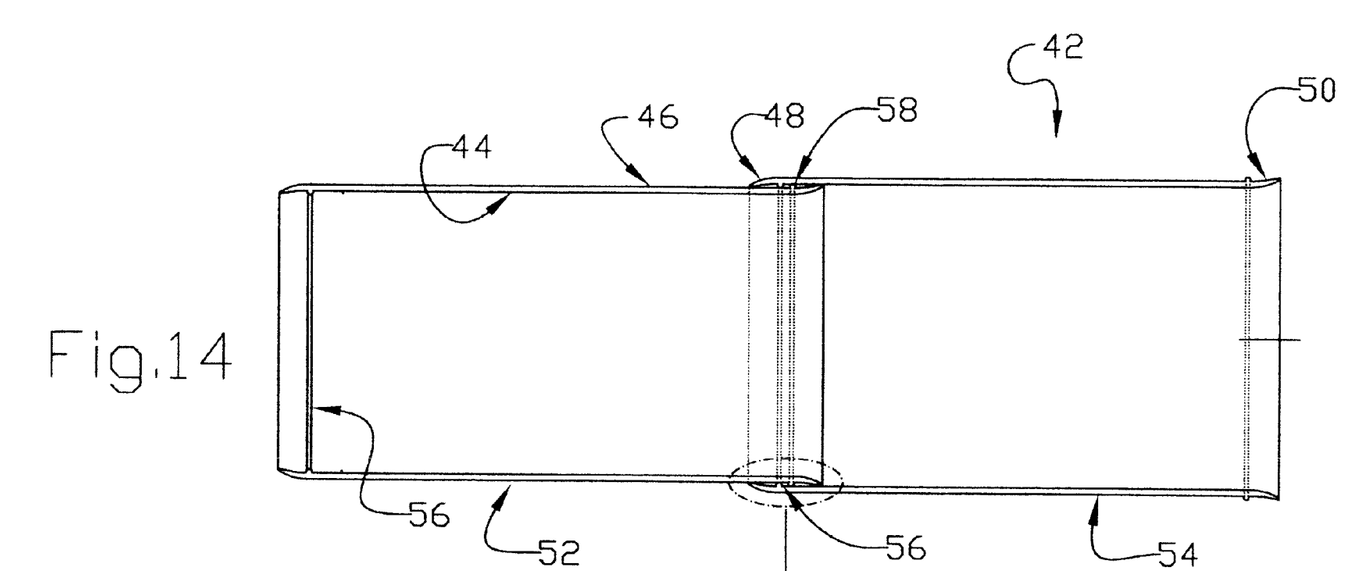
FIG. 14 is a longitudinal cross-sectional view of two sections of the container of the present invention.
Figure 14A:
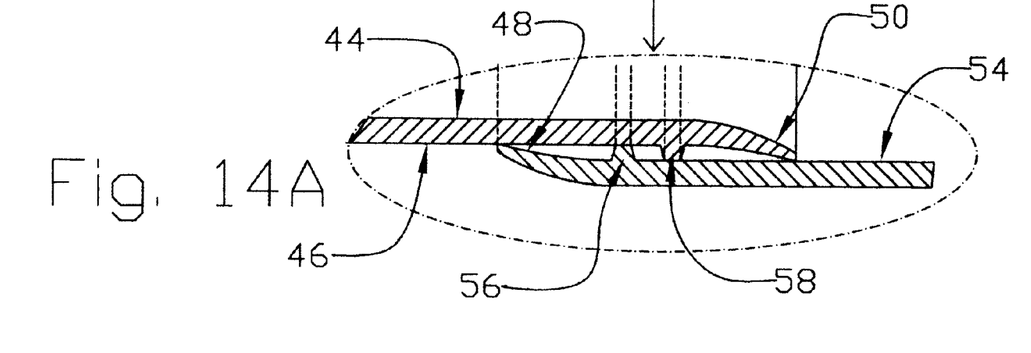
FIG. 14A is a detail view of the junction of two sections of the container as shown in FIG. 14.

With reference to FIGS. 14 and 14A, the configuration of the junctions between the telescopic sections 42 will now be explained. Each section 42 has an inner surface 44, an outer surface 46, a rearward end 48, and a forward end 50. FIGS. 14 and 14A illustrate the preferred configuration wherein a rearward section 52 telescopes into the next forward section 54. On the inner surface 34, the inner surface 44 of the forward end 50 of the rearward section 52 tapers outwardly to allow a smooth flow of the viscous material within the container 6 from a rearward section 52 to a forward section 54. On the outer surface 36, the outer surface 46 of the rearward end 48 of the next forward section 54 taper inwardly to allow a smooth flow of viscous material along the outer surface 36 of the container 6.

The inner surface 44 of the forward section 54 contains a protruding ring 56 near the rearward end 48. The outer surface 46 of the rearward section 52 contains a protruding ring 58 near the forward end 50. The ring 58 of the rearward section 52 is forward of the ring 56 of the forward section 54. These rings 56, 58 prevent separation of the sections 52, 54 and prevent leakage into or out of the container 6.

The circular rearward end 38 of the container 6 is in slidable contact with the circular recess 60 on the forward surface 62 of the thrust wall 22. The thrust wall 22 has a rearward surface 64 against which the piston will push to force the viscous materials out of the cartridge 4 and the container 6. The outer side surface 66 of the thrust wall 22 is cylindrical in shape and fits flush with the inner surface 10 of the cartridge 4. The forward surface 62 of the thrust wall 22 has a circular recess 60 which captures the side walls 32 of the container 6 as the thrust wall 22 moves forward upon being impelled by the piston.

Figure 1:
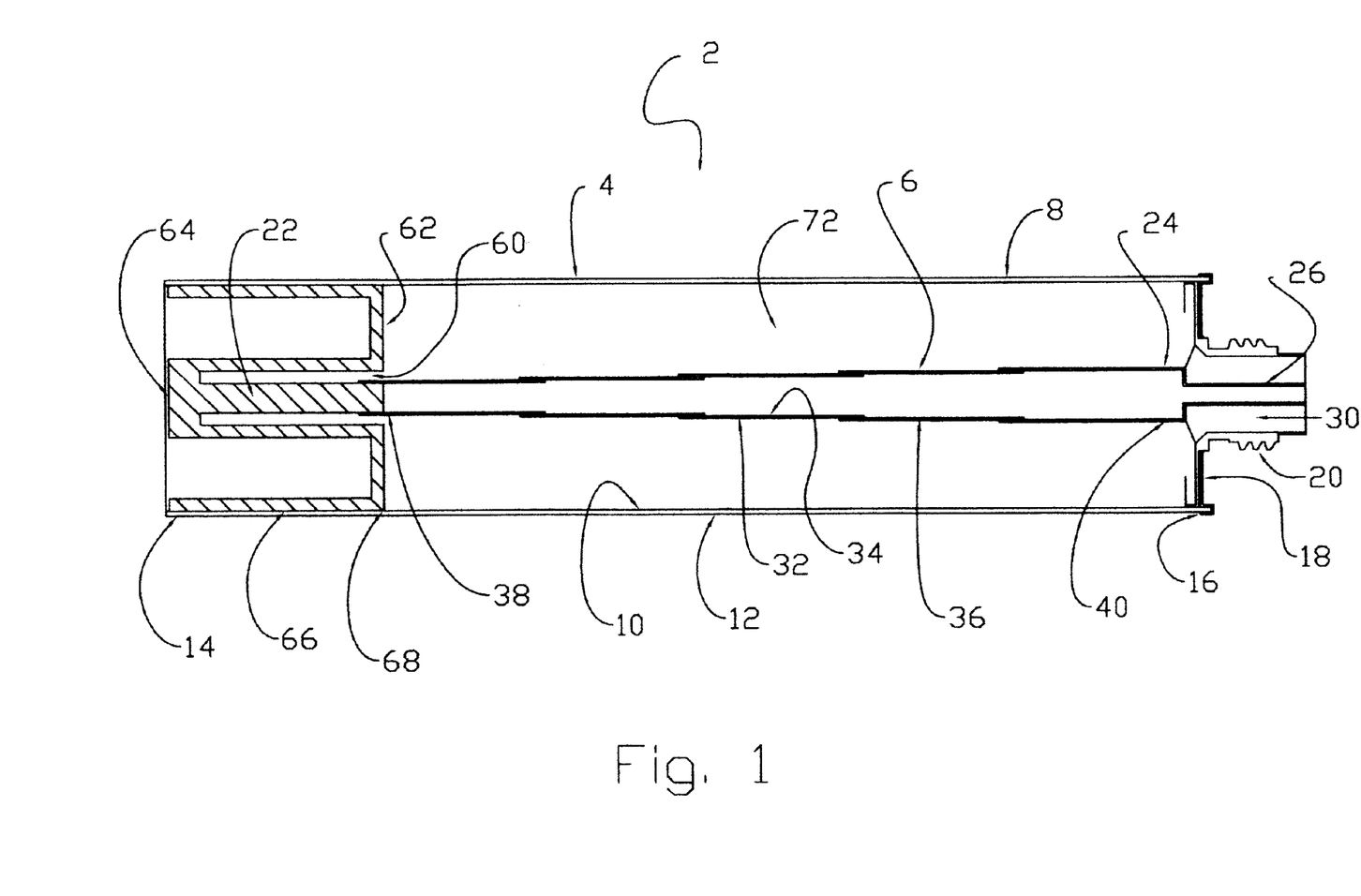
FIG. 1 is a longitudinal cross-sectional view of a dispenser of the present invention having a cartridge and a single full container, the ratio of the volume of the contents within the container to the volume of the contents outside the container being 1:1.
Figure 4:
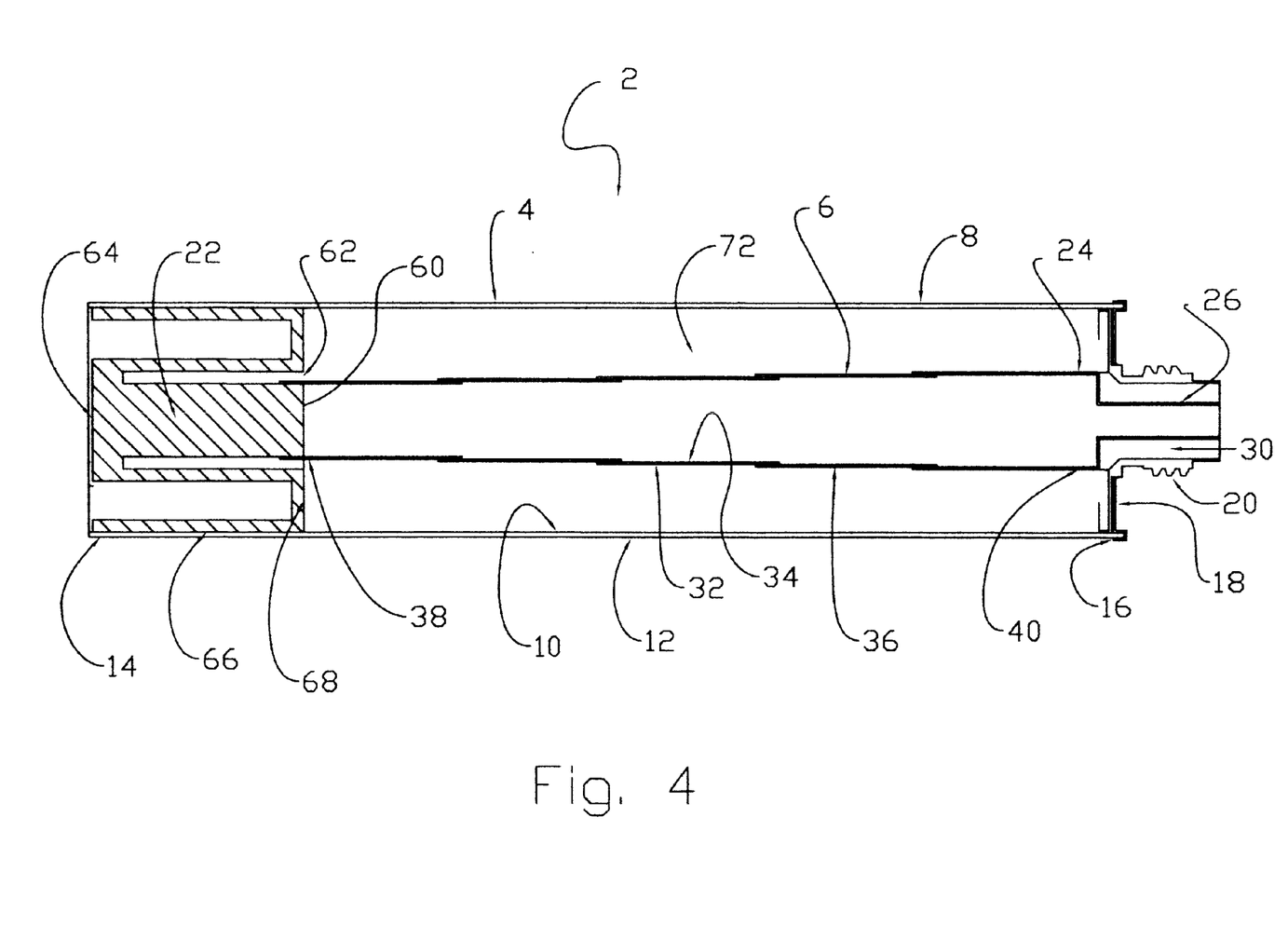
FIG. 4 is a longitudinal cross-sectional view of a dispenser of the present invention having a cartridge and a single full container, the ratio of the volume of the contents within the container to the volume of the contents outside the container being 1:5.
Figure 7:
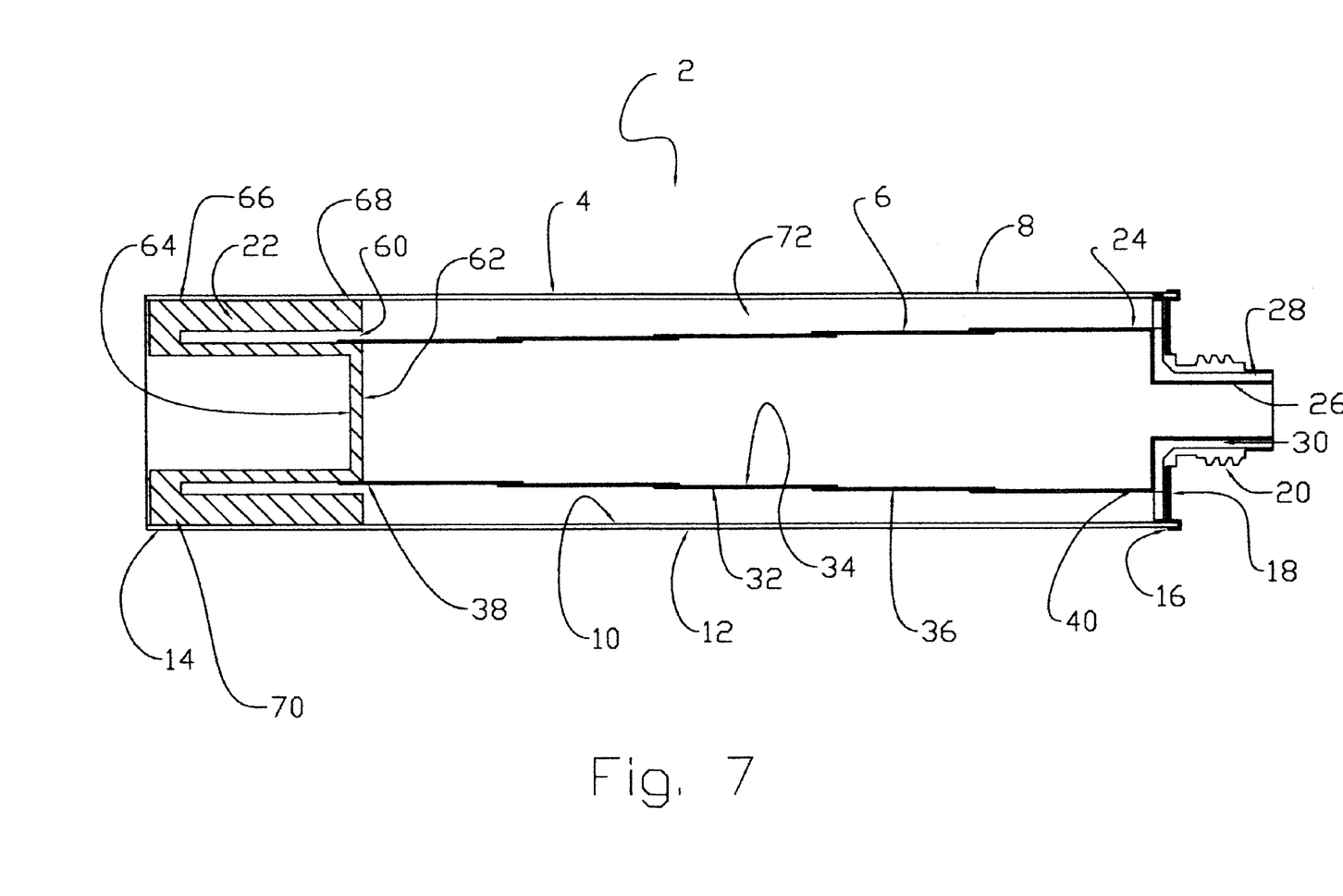
FIG. 7 is a longitudinal cross-sectional view of a dispenser of the present invention having a cartridge and a single full container, the ratio of the volume of the contents within the container to the volume of the contents outside the container being 1:20.

The operation of a dispenser 2 having a single container 6 will now be described with reference to FIGS. 1–9. FIGS. 1, 4, and 7 illustrate dispensers 2 wherein the container 6 is filled with one viscous material and the space 72 between the container 6 and the cartridge 4 is filled with another viscous material. These viscous materials should be kept apart during storage to prevent chemical reaction, but should be brought together in a specific ratio during use in order to react at the proper time. FIG. 1 shows a full dispenser 2 wherein the ratio of volume of viscous material within the container 6 to the volume of viscous material in the space 72 between the container 6 and the cartridge 4 is 1:1. FIG. 4 shows a full dispenser 2 wherein this ratio is 1:5. FIG. 7 shows a full dispenser 2 wherein this ratio is 1:20.

In FIG. 1, the piston will contact the rearward surface 64 of the thrust wall 22 near the forward end 68 of the thrust wall. In FIGS. 4 and 7, the piston will contact the rearward surface 64 of the thrust wall 22 at the rearward end 70 of the thrust wall 22.

As the piston forces the thrust wall 22 forward, both viscous materials are forced out of the dispenser 2 where they will be mixed in a conventional mixing nozzle (not shown). As the thrust wall 22 moves forward, a rearward section 42 of the container 6 slides into the next adjacent forward section 42 so that the forward section 42 ends up in the recess 60 of the thrust 22 wall laterally adjacent the rearward section 42.

Figures 2, 3:
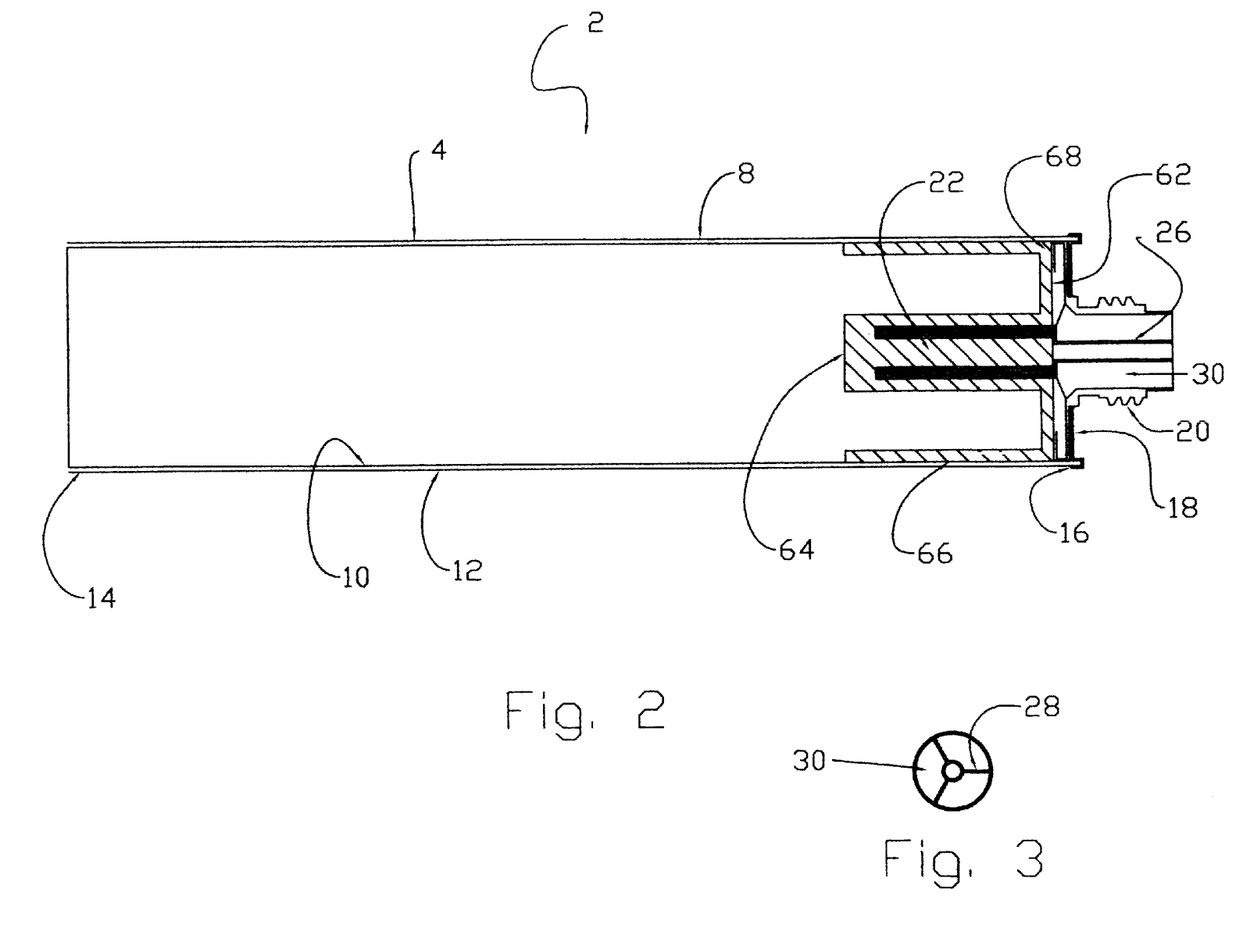
FIG. 2 is a longitudinal cross-sectional view of a dispenser of the present invention having a cartridge and a single container which have been emptied, the ratio of the volume of the contents within the container to the volume of the contents outside the container originally being 1:1.
FIG. 3 is a cross-sectional view through the neck of the dispenser shown in FIGS. 1 and 2.
Figures 5, 6:
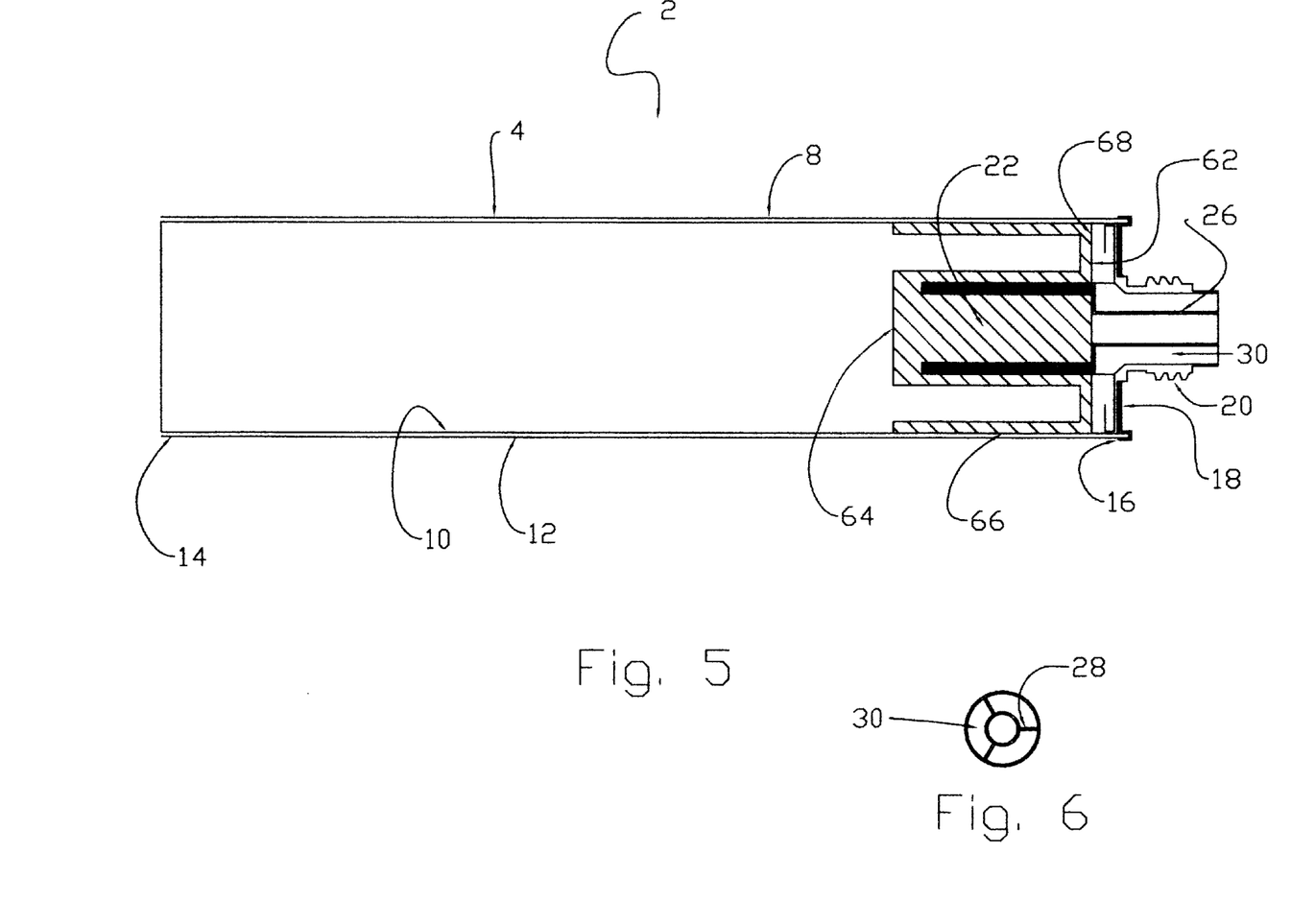
FIG. 5 is a longitudinal cross-sectional view of a dispenser of the present invention having a cartridge and a single container which have been emptied, the ratio of the volume of the contents within the container to the volume of the contents outside the container originally being 1:5.
FIG. 6 is a cross-sectional view through the neck of the dispenser shown in FIGS. 4 and 5.
Figures 8, 9:
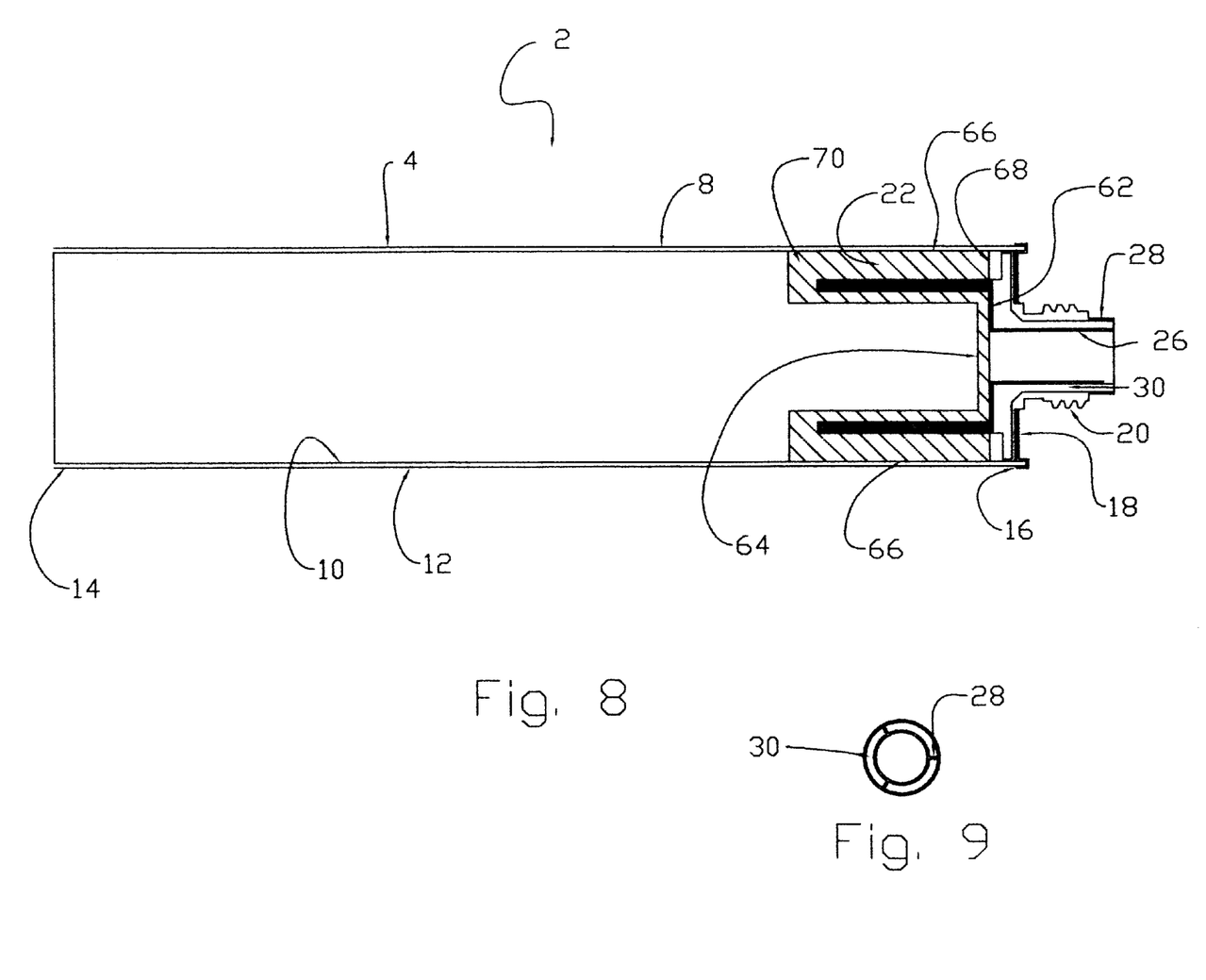
FIG. 8 is a longitudinal cross-sectional view of a dispenser of the present invention having a cartridge and a single container which have been emptied, the ratio of the volume of the contents within the container to the volume of the contents outside the container originally being 1:20.
FIG. 9 is a cross-sectional view through the neck of the dispenser shown in FIGS. 7 and 8.

FIGS. 2, 5, and 8 show dispensers 2 corresponding to FIGS. 1, 5, and 7, respectively, after the viscous materials have been emptied. It is seen that the length of the recess 60 in the thrust wall 22 is the same length as a section 42 of the container 6. This allows the entire container 6 to telescope so that it is captured by the recess 60. When this occurs, all of the material in the container 6 and the space 72 between the container 6 and the cartridge 4 will empty into the neck of the dispenser and will have been dispensed in the desired ratio.

Reference will now be made to FIGS. 10–13 to describe dispensers 2 having multiple containers 6.

Figure 10:
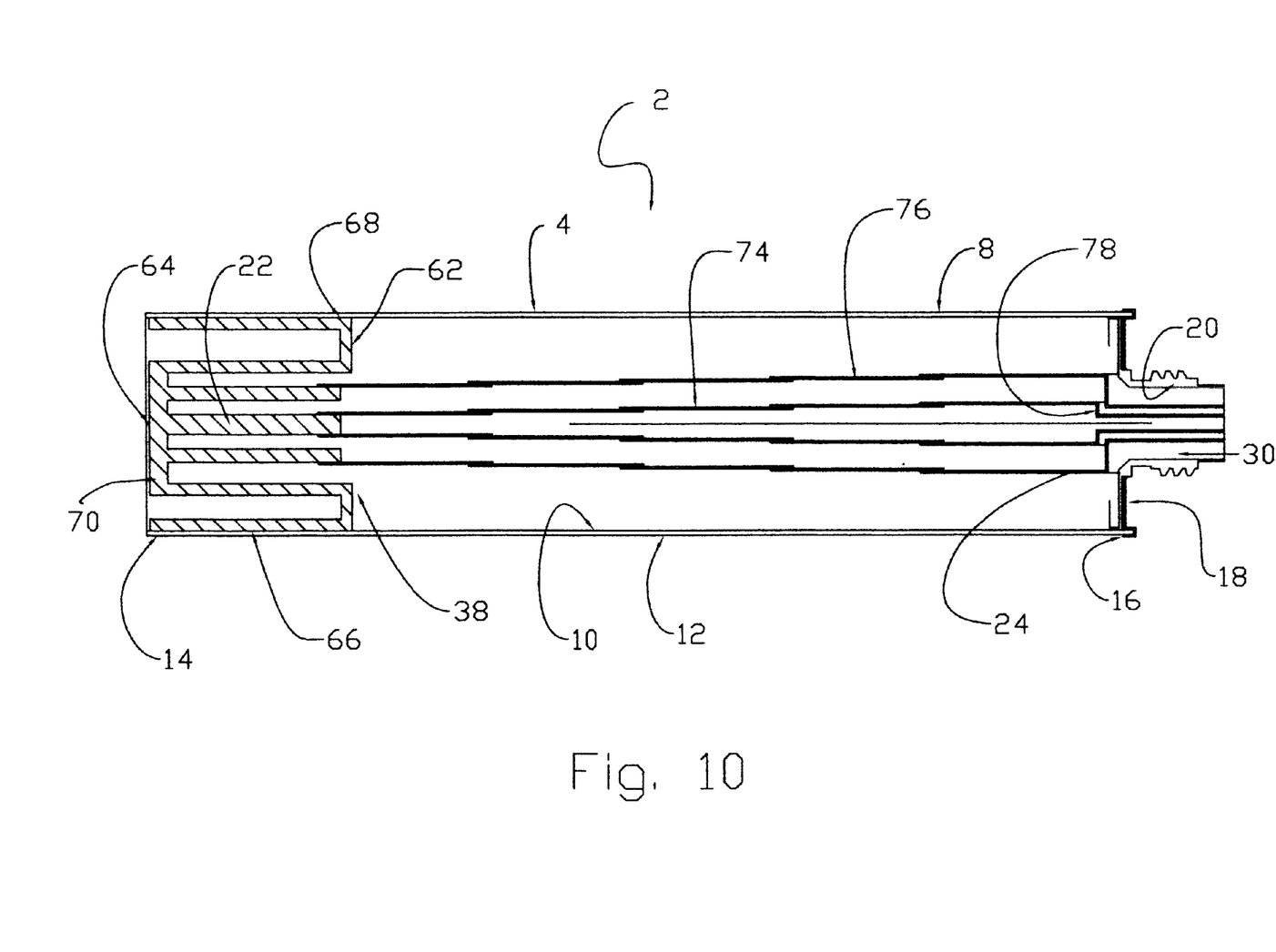
FIG. 10 is a longitudinal cross-sectional view of a dispenser of the present invention having a cartridge and two full concentric containers, the ratio of the volume of the contents within the containers to the volume of the contents outside the containers being 1:5:25.

There are occasions when three or more viscous materials are desired to be mixed to form a final composition and these viscous materials should be kept separate during storage prior to use. FIG. 10 illustrates a full dispenser 2 having a cartridge 4, a concentric inner container 74, and a concentric outer container 76.

As above, the cartridge 4, which is preferably circular in cross-section, has a cylindrical side wall 8 having an inner surface, 10 an outer surface 12, a rearward end 14, and a forward end 16. The forward end 16 has a closed periphery 18 and an open central nozzle 20. The cartridge 4 has an open rearward end 14 containing a slidable rear thrust wall 22.

Each of the inner 74 and outer 76 containers has a forward end 24 which has a neck 26. Each neck 26 fits snugly into an open spacer 28 which, in turn, fits into the open central nozzle 20 of the cartridge 4 in such a manner that there is an open space 30 between the neck 26 of the inner container 74 and the neck 26 of the outer container 76 and an open space 30 between the neck 26 of the outer container 76 and the open central nozzle 20 of the cartridge 4. The forward ends 24 of the containers 74, 76 have closed peripheries 78.

The construction of the walls 32 of each of the inner 74 and outer 76 concentric containers is the same as that described above for a single container 6.

The rearward end 38 of each of the containers 74, 76 is in slidable contact with a recess 60 on the forward surface 62 of the thrust wall 22. The rearward surface 64 and the outer side surface 66 of the thrust wall 22 are as described above. The thrust wall 22 has at least two circular recesses 60 which capture the sectional walls 32 of the containers 6 as the thrust wall 22 moves forward upon being impelled by the piston.

The operation of a dispenser 2 having multiple containers 6 will now be discussed with reference to FIGS. 10–13. FIG. 10 illustrates a dispenser 2 wherein the two concentric containers 74, 76 are filled with two separate viscous materials and the space between the outer container 76 and the cartridge 4 is filled with another viscous material. These viscous materials should be kept apart during storage to prevent chemical reaction, but should be brought together in a specific ratio during use in order to react at the proper time. FIG. 10 shows a full dispenser 2 wherein the ratio of volume of viscous material within the inner container 74 to the volume of viscous material in the outer container 76 to the volume of the viscous material in the space 72 between the outer container 76 and the cartridge 4 is 1:5:25.

Figure 11:
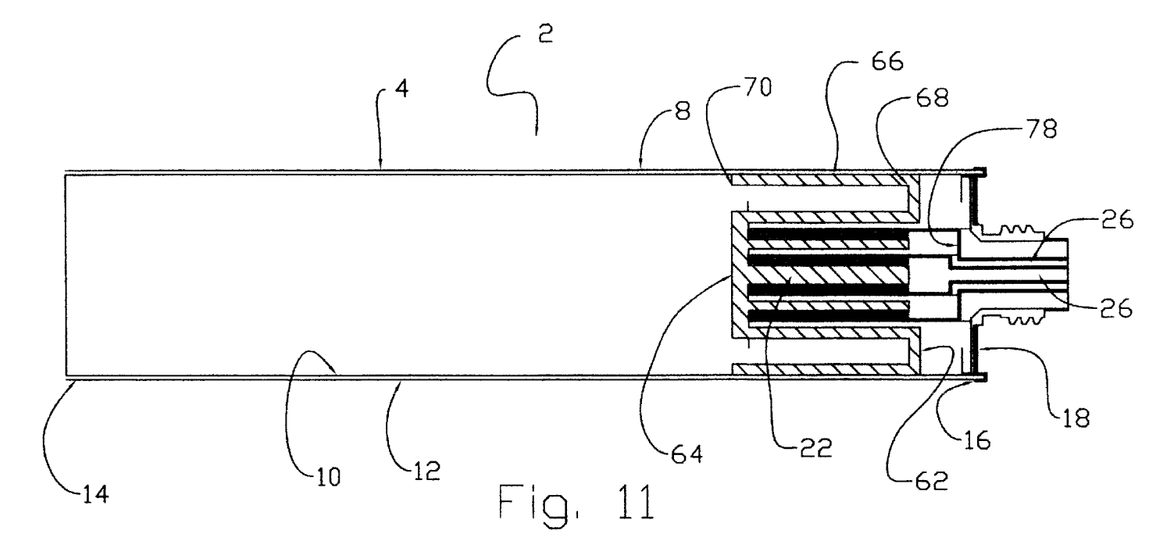
FIG. 11 is a longitudinal cross-sectional view of a dispenser of the present invention having a cartridge and two full concentric containers, which dispenser has been emptied, the ratio of the volume of the contents within the containers to the volume of the contents outside the containers originally being 1:5:25.
Figure 12:
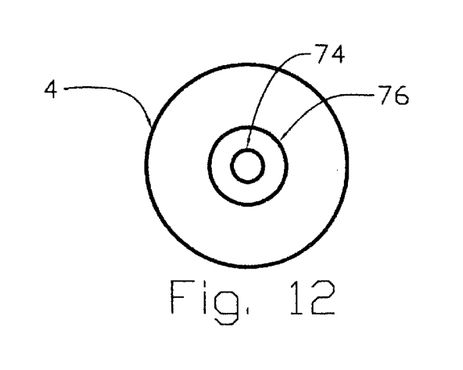
FIG. 12 is a cross-sectional view of the dispenser of 10.
Figure 13:
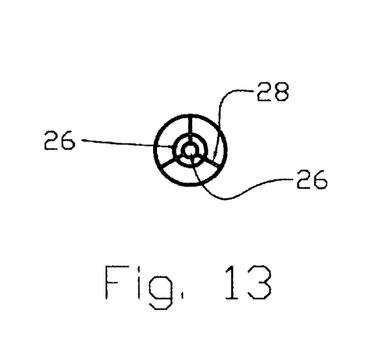
FIG. 13 is a cross-sectional view through the neck of the dispenser shown in FIGS. 10 and 11.

In operation, the piston will contact the rearward surface 64 of the thrust wall 22. As the piston forces the thrust wall 22 forward, the viscous materials are forced out of the dispenser 2 where they will be mixed in a conventional mixing nozzle (not shown). As the thrust wall 22 moves forward, the forward surface 62 of the thrust wall 22 slides into rearward sections 42 of the inner 74 and outer 76 concentric containers. As the thrust wall 22 is forced further forward, rearward sections 42 of the concentric containers 74, 76 slide into the next adjacent forward sections 42 so that the forward sections 42 end up in the recesses 60 of the thrust wall 22 laterally adjacent the rearward sections 42.

FIG. 11 shows the dispenser 2 of FIG. 10 after the viscous materials have been emptied. It is seen that the lengths of the recesses 60 in the thrust wall 22 are the same length as single sections 42 of the concentric containers 74, 76. This allows the entire containers 74, 76 to telescope so that they are captured by the recesses 60. When this occurs, all of the material in the containers 74, 76 and the space 72 between the outer container 76 and the cartridge 4 will empty into the neck of the dispenser 2 and will have been dispensed in the desired ratios.

Although the invention has been described and illustrated in detail, it is to be clearly understood that the same is by way of illustration and example, and is not to be taken by way of limitation. The spirit and scope of the present invention are to be limited only by the terms of the appended claims.

I claim:

1. In a dispenser for viscous materials which should be kept separate until the time of application, the improvement wherein the dispenser comprises:

a) a cartridge having i) a side wall having an inner surface and an outer surface, ii) a rearward end, iii) a forward end, the forward end having a closed periphery and an open central nozzle, iv) an open rearward end for receiving a piston of a dispensing gun, and v) a rear thrust wall which drives the contents of the dispenser forward as the thrust wall is forced forward by the piston, the thrust wall having a rearward surface, an outer side surface which fits flush with the inner surface of the cartridge, and a forward surface having at least one recess; and b) at least one container having i) a forward end having a neck which fits into the open central nozzle of the cartridge and a closed periphery; ii) a side wall having an inner surface, an outer surface, a rearward end, and a forward end, the container comprising multiple telescopic sections, the rearward end of the at least one container being in slidable contact with the at least one recess of the forward surface of the thrust wall such that the at least one recess captures the sectional wall of the at least one container as the thrust wall moves forward.

2. The dispenser of claim 1, wherein the cartridge and the container are cylindrical.

3. The dispenser of claim 2, wherein the container has a forward end which has a neck, which neck fits snugly into an open spacer which, in turn, fits into the open central nozzle of the cartridge in such a manner as to leave an open space between the neck of the container and the open central nozzle of the cartridge.

4. The dispenser of claim 2, wherein there is a single container within the cartridge.

5. The dispenser of claim 2, wherein there are multiple concentric containers within the cartridge.

6. The dispenser of claim 2 wherein a section of the container which is most forward has a diameter larger than the remaining sections of the container and a rearward section telescopes into the next forward section.

7. The dispenser of claim 6 wherein each section of the container has an inner surface, an outer surface, a rearward end, and a forward end and the inner surface of the forward end of the rearward section tapers outwardly and the outer surface of the rearward end of the forward section taper inwardly.

8. The dispenser of claim 7 wherein the inner surface of the forward section contains a protruding ring near the rearward end, the outer surface of the rearward section contains a protruding ring near the forward end, and the ring of the rearward section is forward of the ring of the forward section.

* * * * *